(12) United States Patent
Schickaneder et al.

(10) Patent No.: US 6,599,885 B2
(45) Date of Patent: Jul. 29, 2003

(54) DERIVATIVES OF ERYTHROMYCIN, CLARITHROMYCIN, ROXITHROMYCIN OR AZITHROMYCIN WITH ANTIBIOTIC AND MUCOLYTIC ACTIVITY

(75) Inventors: Helmut Schickaneder, Cork (IE); Aggelos Nikolopoulos, Cork (IE); Gesine Hermann, Cork (IE)

(73) Assignee: Russinsky Limited, Cork (IE)

( * ) Notice: Subject to any disclaimer, the term of this patent is extended or adjusted under 35 U.S.C. 154(b) by 0 days.

(21) Appl. No.: 09/837,416

(22) Filed: Apr. 19, 2001

(65) Prior Publication Data

US 2001/0031736 A1 Oct. 18, 2001

Related U.S. Application Data

(63) Continuation of application No. PCT/IE99/00106, filed on Oct. 15, 1999.

(30) Foreign Application Priority Data

Oct. 20, 1998 (IE) .............................. 1998/0869
Dec. 17, 1998 (IE) .............................. 1998/1062

(51) Int. Cl.[7] .................. A61K 31/70; C07H 17/08
(52) U.S. Cl. ......................... 514/29; 536/7.2; 536/7.4
(58) Field of Search ..................... 536/7.2, 7.4; 514/29

(56) References Cited

U.S. PATENT DOCUMENTS 4,476,120 A  10/1984  Gonella

FOREIGN PATENT DOCUMENTS

| EP | 0005789 B1 | 5/1981 |
|---|---|---|
| EP | 0057489 | 2/1982 |
| EP | 0052909 A1 | 6/1982 |
| EP | 0052910 A1 | 6/1982 |
| EP | 0096013 A1 | 12/1983 |
| WO | WO96/19489 | 6/1996 |
| WO | WO98/05674 | 2/1998 |

OTHER PUBLICATIONS

Bernardi et al, Clinical Pharmacology Therapy and Toxicology, vol. 6, No. 9, "Human Pharmacokinetics . . . ", pp. 444–447, Sep. 1, 1988.

Pomarelli, IL FARMACO, vol. 33, No. 9, "Studio farmacologico di un'associazione antibiotico–mucolitica", pp. 379–391, Sep. 1978.

*Primary Examiner*—Elli Peselev
(74) *Attorney, Agent, or Firm*—Jacobson Holman PLLC

(57) ABSTRACT

A pharmaceutical with an enhanced pharmaceutical profile comprises a mucolytic and an antibiotic in which the mucolytic is present in an amount of greater than one molar equivalent of the antibiotic. The antibiotic may be selected from Erythromycin, Roxithromycin, Clarithromycin, Azithromycin, Dirithromycin; and pharmaceutically acceptable salts or esters thereof. The mucolytic is a mucolytically active thiol, especially N-acetylcysteine, mercaptoethanesulfonic acid, tiopronin or methylcysteine. The adducts can be isolated via a simple and efficient process.

28 Claims, No Drawings

DERIVATIVES OF ERYTHROMYCIN, CLARITHROMYCIN, ROXITHROMYCIN OR AZITHROMYCIN WITH ANTIBIOTIC AND MUCOLYTIC ACTIVITY

This is a Continuation Application of PCT International Application No. PCT/IE99/00106, filed Oct. 15, 1999.

The invention relates to a pharmaceutical including a macrolide antibiotic. The invention also relates to a process for manufacturing the pharmaceutical.

The compounds Erythromycin, Roxithromycin, Clarithromycin, Azithromycin and Dirithromycin are widely used macrolide antibiotics for the treatment of various types of infections. The chemical structures of these macrolides as follows.

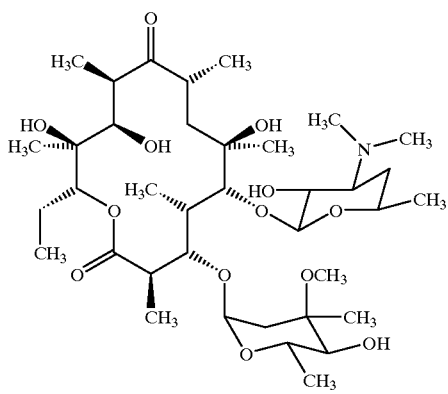

Erythromycin A

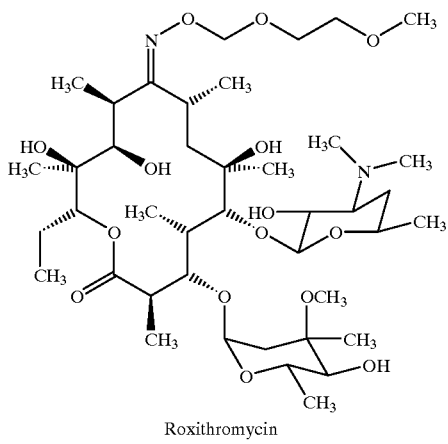

Roxithromycin

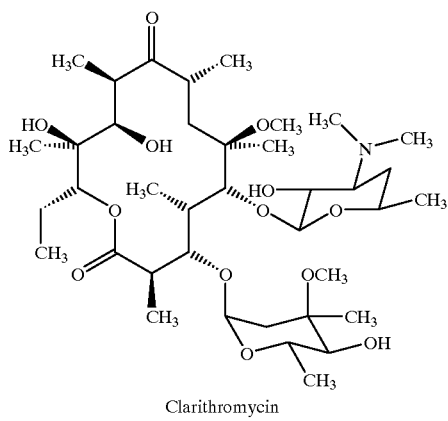

Clarithromycin

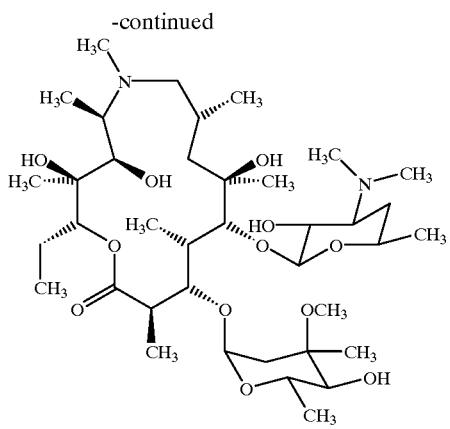

Azithromycin

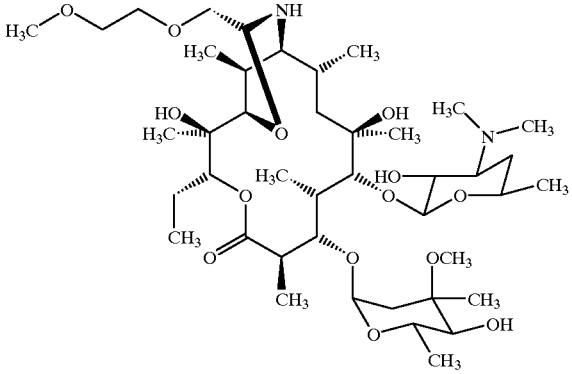

Dirithromycin

It is known that the stability and the pharmacological and immunomicrobiological profile of these compounds can be improved by derivatisation and by conversion into various salts.

EP-A-0057489 describes salts of Erythromycin and Erythromycin propionate with N-acetylcysteine, carboxymethylcysteine, thiazolidin-carboxylic acid and mercapto-succinic acid. However these salts are sensitive to sunlight, humidity and heat.

WO-A-96/19489 describes a salt of Roxithromycin with N-acetylcysteine.

There is a need for a pharmaceutical including a macrolide antibiotic which will have an enhanced pharmaceutical profile.

STATEMENTS OF THE INVENTION

According to the invention there is provided a pharmaceutical comprising:
 a mucolytic and
 an antibiotic, pharmaceutically acceptable salts or esters thereof,
 wherein the mucolytic is present in an amount of greater than one molar equivalent of the antibiotic.

In a preferred embodiment of the invention the antibiotic is selected from:
 Erythromycin;
 Roxithromycin;
 Clarithromycin;
 Azithromycin;
 Dirithromycin; and
 pharmaceutically acceptable salts or esters thereof.

Preferably the mucolytic is a mucolytically active thiol. Usually the mucolytically active thiol is selected from:

N-acetylcysteine;

mercaptoethanesulfonic acid;

tiopronin; and methylcysteine.

Preferably the mucolytic is present in an amount of less than about four molar equivalents of the antibiotic. Most preferably the mucolytic is present in an amount of less than two molar equivalents of the antibiotic.

In a preferred embodiment of the invention the pharmaceutical includes a compound of the formula $$[RH^{\oplus}][X^{\ominus}]$$

wherein
R is a radical selected from:
Erythromycin;
Clarithromycin;
Roxithromycin;
Azithromycin;
Dirithromycin;
pharmaceutically acceptable esters thereof; and
HX is a mucolytically active thiol.

In one embodiment of the invention the pharmaceutical includes a compound of the formula $$[RH^{\oplus}][Y^{\ominus}]$$

wherein
R is as defined above and
HY is a pharmaceutically acceptable inorganic or organic acid.

In another embodiment of the invention the pharmaceutical includes a compound of the formula:

$$[RH^{\oplus}(HX^*)_n][X^{\ominus}]$$

wherein
R and HX are as defined above,
HX* is a bound mucolytically active thiol; and
n is a number greater than zero.
For example n may be 1, 2 or 3.

The invention also provides a pharmaceutical including a compound of the formula $$[RH^{\oplus}(HX^*)][X^{\ominus}]$$

and compounds of the formulae:

$$[RH^{\oplus}(HX^*)_2][X^{\ominus}]$$

$$[RH^{\oplus}(HX^*)_3][X^{\ominus}]$$

wherein R, HX and HX* are as defined above.

The pharmaceutical may include a compound of the formula:

$$[RH^{\oplus}(HX^*)_n][Y^{\ominus}]$$

wherein
R and HX* are as defined above;
HY is a pharmaceutically acceptable inorganic or organic acid; and
n is a number greater than zero.
For example n may be 1, 2 or 3.

In a preferred embodiment of the invention the pharmaceutical includes a compound of the formula:

$$[RH^{\oplus}(HX^*)][Y^{\ominus}]$$

and compounds of the formulae:

$$[RH^{\oplus}(HX^*)_2][Y^{\ominus}]$$

$$[RH^{\oplus}(HX^*)_3][Y^{\ominus}]$$

wherein R, HX* and HY are as defined above.

The invention also provides a compound of the formula:

$$[RH^{\oplus}(HX^*)_n][X^{\ominus}]$$

wherein R, HX, HX* and n are as defined above.

The invention further provides a compound of the formula:

$$[RH^{\oplus}(HX^*)][X^{\ominus}]$$

wherein R, HX and HX* are as defined above.

In addition, the invention provides compounds of the formulae:

$$[RH(HX^*)_2][X]$$

$$[RH(HX^*)_3][X]$$

wherein R, HX and HX* are as defined above.

The invention also provides a compound of the formula:

$$[RH^{\oplus}(HX^*)_n][X^{\ominus}]$$

wherein R, HX*, HY and n are as defined above.

The invention also provides a compound of the formula:

$$[RH^{\oplus}(HX^*)][Y^{\ominus}]$$

wherein R, HX* and HY are as defined above.

The invention further provides compounds of the formulae:

$$[RH^{\oplus}(HX^*)_2][Y^{\ominus}]$$

$$[RH^{\oplus}(HX^*)_3][Y^{\ominus}]$$

wherein R, HX* and HY are as defined above.

The invention also provides a process for preparing a compound of the formula:

$$[RX^{\oplus}(HX^*)_n][X^{\ominus}]$$

wherein R, HX, HX* and n are as defined above by reacting a compound of the formula R with a desired molar equivalent(s) of a compound of the formula HX.

The process may include the step of forming, as an intermediate, a compound of the formula:

$$[RH][X]$$

wherein R and HX are as defined above.

According to another aspect the invention provides a process for preparing a compound of the formula:

$$[RH^{\oplus}(HX^*)_n][Y^{\ominus}]$$

wherein R, HX*, HY and n are as defined above by reacting a compound of the formula R with a compound of the formula HY to form a compound of the formula:

$$[RH][Y]$$

which is reacted with a desired molar equivalent(s) of a compound of the formula HX wherein R, HX and HY are as defined above.

Preferably the process is carried out in the presence of water.

Ideally the process is carried out at a temperature of from 15 to 45° C., preferably at a temperature of from 20 to 25° C.

In another aspect the invention provides a pharmaceutical composition in solid form incorporating a compound of the invention.

It has surprisingly been found that the pharmacological profile of [1:1] antibiotic-mucolytic agents can be improved. In particular the mucolytic effect can be increased by preparing salts of macrolide antibiotics with an additional amount of mucolytic agent.

It has also surprisingly been found that novel adducts with a molar ratio higher than [1:1] (antibiotic-mucolytic agent) can be isolated via a very simple and efficient process. Such adducts can for example be integer [1:2]-, [1:3]- or [1:4] compounds bearing a one, two or three molar excess of mucolytic relative to the equivalent of antibiotic. Alternatively any type of non-integer adducts in the range between [1:1] and [1:4] may also be prepared.

Especially Erythromycin A or its pharmaceutically acceptable esters, Roxithromycin, Clarithromycin or Azithromycin are suitable to form such an adduct with mucolytically active thiols, in particular with N-acetylcysteine. The reaction is ideally performed under aqueous conditions affording the products in high yield and very good quality.

DETAILED DESCRIPTION

The invention provides novel macrolide antibiotics bearing a mucolytically active component as shown in scheme 2:

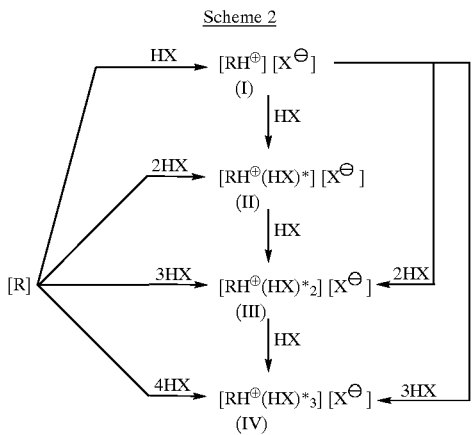

R is a radical preferably selected from Erythromycin A or its pharmaceutically acceptable esters, Clarithromycin, Roxithromycin or Azithromycin.

HX is a mucolytically active thiol, preferably selected from N-acetylcysteine, mercaptoethanesulfonic acid, tiopronin or methylcysteine.

HX* is a bound mucolytically active thiol, preferably N-acetylcysteine, mercaptoethanesulfonic acid, tiopronin or methylcysteine.

R can be converted into its acid-base addition salt (I) by reaction with a mucolytically active thiol HX.

Adduct (II) can be obtained by reacting (I) with a second equivalent of HX; alternatively R can directly be converted into (II) using two equivalents of HX. The formation of compounds (III) and (IV) may be achieved by direct reaction of R with 3 or 4 equivalents of HX. Alternatively stepwise conversion may be performed by reacting R portion wise with HX as outlined in scheme 2.

If non-integer equivalents of HX greater than one are used, mixtures of the compounds (I), (II), (III) and (IV) may be isolated depending on the added amount of HX.

Optionally the antibiotic R can initially be reacted with an inorganic or organic acid HY into a pharmaceutically acceptable acid-base addition salt of type:

[RH][Y] 

This salt may then be further converted by reaction with HX into compounds of the following formulae and mixtures thereof:

[RH$^\oplus$(HX)*][Y$^\ominus$] 

[RH$^\oplus$(HX)*$_2$][Y$^\ominus$] 

[RH$^\oplus$(HX)*$_3$][Y$^\ominus$] 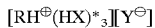

The reaction takes place in an analogous way to the process shown in scheme 2.

The process is preferably performed in the presence of water.

The most preferred mucolytic is N-acetylcysteine.

The invention will be more clearly understood by means of the following examples:

GENERAL PROCEDURE

The macrolide antibiotic and the mucolytic are homogenised for 1–2 h preferably at room temperature. Process water is then added and homogenisation is continued for 1–2 h at a temperature of 15–45° C., preferably at 20–25° C. The product is dried under vacuum and isolated in quantitative yield. Optionally the product may be milled. The process may, for example, be carried out using an INOX dryer as described in WO-A-9619489.

EXAMPLE 1

Preparation of Erythromycin Propionate-N-Acetylcysteine-[1:1]-Salt

Used materials:
5.38 kg Erythromycin Propionate
1.11 kg N-acetylcysteine
1–2 l process water The reaction is carried out according to the general procedure.

Melting range: 103–128° C.

FT-IR (KBr): ν[cm$^1$]=3450, 2974, 2940, 1737, 1653, 1464, 1377, 1169, 1084, 1056, 1009.

$[\alpha]_D^{20}$: −57.2° (c=10.00 in ethanol).

Powder X-ray peaks of medium to high intensity: 2θ=9.18, 16.70, 18.33, 19.25.

EXAMPLE 2

Preparation of Erythromycin Propionate-N-Acetylcysteine [1:1.8]-Adduct

Used materials:
5.38 kg Erythromycin Propionate
2.00 kg N-acetylcysteine
300–600 ml process water, preferably 350–450 ml The reaction is carried out according to the general procedure.

Melting range: 114–124° C.

FT-IR (KBr): 3466, 2974, 2941, 1738, 1464, 1378, 1169, 1083, 1053.

$[\alpha]_D^{20}$: −48.5° (c=9.99 in ethanol).

Powder X-ray peaks of medium and high intensity: 2θ=5.17, 9.10, 14.01, 16, 24, 22.89, 49.73.

EXAMPLE 3

Preparation of Erythromycin Propionate-N-Acetylcysteine [1:3]-Adduct

Used materials:
  5.38 kg Erythromycin Propionate
  3.33 kg N-acetylcysteine
  300–600 ml process water, preferably 350–450 ml The reaction is carried out according to the general procedure.
Melting range: 109–119.5° C.
FT-IR (KBr): 3469, 2974, 2941, 1737, 1464, 1377, 1169, 1084, 1053.
$[\alpha]_D^{20}$: −38.3° (c=10.35 in ethanol).
Powder X-ray peaks of medium and high intensity: $2\theta$=5.25, 9.20, 16.34, 20.13, 28.64, 30.16.

EXAMPLE 4

Preparation of Erythromycin Propionate-N-Acetylcysteine [1:4]-Adduct

Used materials:
  5.38 kg Erythromycin Propionate
  4.44 kg N-acetylcysteine
  300–600 ml process water, preferably 350–450 ml The reaction is carried out according to the general procedure.
Melting range: 110–118° C.
FT-IR (KBr): 3473, 2974, 1738, 1464, 1379, 1168, 1084, 1053.
$[\alpha]_D^{20}$: −31.1° (c=10.08 in ethanol).
Powder X-ray peaks of medium and high intensity: $2\theta$=4.91, 8.86, 15.99, 26.33, 59.07.

EXAMPLE 5

Preparation of Roxithromycin-N-Acetylcysteinate-[1:1]-Salt

Used materials:
  1.80 kg Roxithromycin
  351 g N-acetylcysteine
  600–800 ml process water, preferably 700–750 ml The reaction is carried out according to the general procedure.
Melting range: 95–100° C.
FT-IR (KBr): $\nu[cm^{-1}]$=3456, 2971, 1735, 1636, 1602, 1465, 1384, 1280, 1169, 1078, 1012.

EXAMPLE 6

Preparation of Clarithromycin-N-Acetylcysteinate-[1:1]-Salt

Used materials:
  3.60 kg Clarithromycin
  0.77 kg N-acetylcysteine
  300–600 ml process water, preferably 350–450 ml The reaction is carried out according to the general procedure.
Melting range: 173.5–183° C.
FT-IR (KBr): $\nu[cm^{-1}]$=3478, 2976, 1732, 1693, 1463, 1380, 1348, 1268, 1170, 1110, 1052, 1011.
$[\alpha]_D^{20}$: −72.22° (c=10.09).
Powder X-ray peaks of medium and high intensity: $2\theta$=6.30, 9.89, 11.58, 11.91, 13.82, 15.34, 15.94, 18.69, 22.36, 28.20.

EXAMPLE 7

Preparation of Clarithromycin-N-Acetylcysteinate-[1:4]-Salt

Used materials:
  3.60 kg Clarithromycin
  3.00 kg N-acetylcysteine
  300–600 ml process water, preferably 350–450 ml The reaction is carried out according to the general procedure.
Melting range: 110–118° C.
FT-IR (KBr): $\nu[cm^{-1}]$=3473, 2974, 2939, 1733, 1693, 1462, 1379, 1347, 1285, 1169, 1110, 1053, 1011.
$[\alpha]_D^{20}$: −38.60° (c=9.99 in ethanol).
Powder X-ray peaks of medium and high intensity: $2\theta$=6.34, 9.80, 13.77, 14.94, 15.93, 18.56.

Salts with other ratios of antibiotic and N-acetylcysteine of Erythromycin, Roxithromycin, Clarithromycin, Azithromycin or Dirithromycin may be prepared in an analogous way.

The same procedure may also apply to the preparation of adducts of antibiotics and mucolytically active agents other than N-acetylcysteine.

Antibiotic Activity

*Micrococcus luteus* from stock was streaked on a nutrient agar plate to confirm colony morpbiology, colour and purity. After 24 hours incubation at 37° C. an isolated colony is picked and inoculated into 10 ml of nutrient broth. This is incubated overnight at 37° C. and is subsequently used as the inoculum. 10 mg of each of the test compounds is weighed and dissolved in 10 ml of analar methanol in sterile 20 ml universal containers. This is then diluted with ringers buffer solution to give a concentration of 1 mg/ml.

Quantitation of activity is determined using an MIC (Mean Inhibitory Concentration) liquid tube assay. For each test substance the following concentrations are set up: 10 µg/ml, 5 µg/ml, 1 µg/ml, 0.5 µg/ml, 0.1 µg/ml, 0.05 µg/ml and 0.01 µg/ml. Each contained nutrient broth and 0.1 ml of overnight culture of *Micrococcus luteus*.

The tubes were incubated at 37° C. and observed for growth after 24 hours and 48 hours. Growth is assessed by dense turbidity, optical density at 660 nm using a spectrophotometer or clarity. The MIC is the last concentration where growth inhibited.

The following table gives the MIC values for the compounds examined:

| Compound | MIC [µg/ml] |
| --- | --- |
| Erythromycin-propionate | 0.01–0.05 |
| Erythromycin-N-acetylcysteinate [1:1] | 0.01–0.05 |
| Erythromycin-N-acetylcysteinate [1:1.8] | ≦0.01 |
| Erythromycin-N-acetylcysteinate [1:4] | 0.05–0.1 |
| Clarithromycin | ≦0.01 |
| Clarithromycin-N-acetylcysteinate [1:1] | ≦0.01 |
| Clarithromycin-N-acetylcysteinate [1:4] | 0.01–0.05 |

It will be noted that in general the activity of the 1:1 compound is similar to that of the base antibiotic. Surprisingly however the activity increases to an optimum level around 1:2 and then decreases, particularly at 1:4 or greater.

The pharmaceuticals of the invention can be readily formulated into solid dosage forms such as tablets, capsules, suppositories and the like. A single dosage form without any interaction between the individual components is provided. The pharmacological profile is enhanced. There is also the added advantage of patient compliance in that a single drug may be taken to achieve an enhanced effect.

The invention is not limited to the embodiments hereinbefore described which may be varied in detail.

What is claimed is:

1. A pharmaceutical composition comprising
   a mucolytically active thiol selected from the group consisting of: N-acetylcysteine; mercaptoethanesulphonic acid; tiopronin and methylcysteine; and
   an antibiotic selected from the group consisting of: Erythromycin; Roxithromycin; Clarithromycin; Azithromycin; Dirithromycin; and
   pharmaceutically acceptable salts or esters thereof,
   wherein the mucolytic is present in an amount of between 1.8 molar and four molar equivalent of the antibiotic.

2. The pharmaceutical composition of claim 1, wherein the mucolytic is present in an amount of about two molar equivalents of the antibiotic.

3. The pharmaceutical composition of claim 1, which comprises a compound of the formula $$[RH^{\oplus}][X^{\ominus}]$$

wherein R is a radical selected from the group consisting of: Erythromycin; Clarithromycin; Roxithromycin; Azithromycin; Dirithromycin; and pharmaceutically acceptable esters thereof; and
HX is a mucolytically active thiol selected from the group consisting of N-acetylcysteine; mercaptoethanesulphonic acid; tiopronin; and methylcysteine,
wherein the mucolytically active thiol is present in an amount of between 1.8 molar and four molar equivalents of the antibiotic.

4. The pharmaceutical composition of claim 1, wherein the antibiotic is a compound of the formula $$[RH^{\oplus}][Y^{\ominus}]$$

wherein R is a radical selected from the group consisting of Erythromycin; Clarithromycin; Roxithromycin; Azithromycin; Dirithromycin; and pharmaceutically acceptable esters thereof; and
HY is a pharmaceutically acceptable inorganic or organic acid.

5. The pharmaceutical composition of claim 1, which comprises a compound of the formula $$[RH^{\oplus}(HX^*)_n][X^{\ominus}]$$

wherein R is Erythromycin, Clarithromycin, Roxithromycin, or Azithromycin;
HX* is a bound mucolytically active thiol selected from the group consisting of N-acetylcysteine; mercaptoethanesulphonic acid; tiopronin; and methylcysteine; and
n is a number between 1.8 and 4 and a pharmaceutically acceptable carrier.

6. The pharmaceutical composition of claim 5, wherein n is 2.

7. The pharmaceutical composition of claim 5, wherein n is 3.

8. The pharmaceutical composition of claim 5, which comprises a compound of the formula $$[RH^{\oplus}(HX^*)_n][X^{\ominus}]$$

and one or more compounds of the formulae:

$$[RH^{\oplus}(HX^*)_2][X^{\ominus}]$$

$$[RH^{\oplus}(HX^*)_3][X^{\ominus}]$$

wherein R and HX* are as defined in claim 5 and n is a number between 1.8 and 4.

9. The pharmaceutical composition of claim 1, which comprises a compound of the formula $$[RH^{\oplus}(HX^*)_n][Y^{\ominus}]$$

wherein
R is Erythromycin, Clarithromycin, Roxithromycin, or Azithromycin;
HX* is a bound mucolytically active thiol selected from the group consisting of N-acetylcysteine; mercaptoethanesulphonic acid; tiopronin; and methylcysteine; and
HY is a pharmaceutically acceptable inorganic or organic acid; and
n is a number between 1.8 and 4.

10. The pharmaceutical composition of claim 9, wherein n is 2.

11. The pharmaceutical composition of claim 9, wherein n is 3.

12. The pharmaceutical composition of claim 9, which comprises a compound of the formula $$[RH^{\oplus}(HX^*)_n][Y^{\ominus}]$$

and one or more compounds of the formulae:

$$[RH^{\oplus}(HX^*)_2][Y^{\ominus}]$$

wherein R, HX*, and HY and n are as defined in claim 9.

13. A pharmaceutical composition comprising
    a mucolytically active thiol selected from the group consisting of N-acetylcysteine; mercaptoethanesulphonic acid; tiopronin; and methylcysteine; and
    an antibiotic selected from the group consisting of Erythromycin; Roxithromycin; Clarithromycin; Azithromycin; Dirithromycin; and pharmaceutically acceptable salts or esters thereof,
    wherein the mucolytic and antibiotic are present in a molar ratio of 1.8:1.

14. A pharmaceutical composition comprising N-acetylcysteine and Erythromycin in a molar ratio of 1.8:1 mucolytic to antibiotic.

15. A compound of the formula $$[RH^{\oplus}(HX^*)_n][X^{\ominus}]$$

wherein R, HX*, and n are as defined in claim 5.

16. A compound of the formula $$[RH^{\oplus}(HX^*)_2][X^{\ominus}]$$

wherein R and HX* are as defined in claim 5.

17. A compound of the formula $$[RH^{\oplus}(HX^*)_3][X^{\ominus}]$$

wherein R and HX* are as defined in claim 5.

18. A compound of the formula $$[RH^{\oplus}(HX^*)_n][Y^{\ominus}]$$

wherein R, HX*, HY, and n are as defined in claim 9.

19. A compound of the formula $$[RH^{\oplus}(HX^*)_2][Y^{\ominus}]$$

wherein R, HX*, and HY are as defined in claim 9.

20. A compound of the formula $$[RH^{\oplus}(HX^*)_3][Y^{\ominus}]$$

wherein R, HX*, and HY are as defined in claim 9.

21. A process for preparing a compound of the formula $$[RH^{\oplus}(HX)^*_n][X^{\ominus}]$$

wherein R, (HX)*, and n are as defined in claim 9 which comprises reacting a compound of the formula [R] with a desired molar equivalent of a compound of the formula [HX].

22. The process of claim 21, which comprises the step of forming, as an intermediate, a compound of the formula $$[RH^{\oplus}][X^{\ominus}]$$

which comprises reacting a compound of the formula [R] with a desired molar equivalent of a compound of the formula [HX]

wherein R is Erithromycin, Clarithromycin, Roxithromycin or Azithromycin; and

HX* is a bound mucolytically active thiol selected from the group consisting of N-acetylcysteine; mercaptoethanesulphonic acid; tiopronin; and methylcysteine.

23. A process for preparing a compound of the formula $$[RH^{\oplus}(HX^*)_n][Y^{\ominus}]$$

wherein R, HX*, and n are as defined in claim 9, which comprises reacting a compound of the formula [R] with a compound of the formula [HY] to form a compound of the formula $$[RH^{\oplus}][Y^{\ominus}]$$

which is reacted with a desired molar equivalent of a compound of the formula [HX] wherein [HY] and [HX] are as defined in claim 9.

24. The process of claim 21, which is carried out in the presence of water.

25. The process of claim 21, which is carried out at a temperature of from 15 to 45° C.

26. The process of claim 21, which is carried out at a temperature of from 20 to 25° C.

27. A pharmaceutical composition in a solid form comprising a compound as claimed in claim 15.

28. A pharmaceutical composition in a solid form comprising a compound as claimed in claim 10.

* * * * *